United States Patent [19]

Blachly

[11] 4,112,936
[45] Sep. 12, 1978

[54] BITE BLOCK ASSEMBLY ADAPTED FOR ADJUSTABLE MOUNTING AND HOLDING OF ORAL AIRWAYS AND METHOD OF USING SAME

[76] Inventor: Paul H. Blachly, 3348 NW Skyline Blvd., Portland, Oreg. 97229

[21] Appl. No.: 726,944

[22] Filed: Sep. 27, 1976

[51] Int. Cl.² .......................................... A61M 16/00
[52] U.S. Cl. ................................... 128/136; 128/208; 128/351
[58] Field of Search ............ 128/136, 208, 147, 145.5, 128/145.8, 351, 12

[56] References Cited

U.S. PATENT DOCUMENTS 2,669,988   2/1954   Carpenter ........................... 128/136

FOREIGN PATENT DOCUMENTS 751,281   6/1956   United Kingdom ..................... 128/136

Primary Examiner—Robert W. Michell
Assistant Examiner—Henry J. Recla
Attorney, Agent, or Firm—Chernoff & Vilhauer

[57] ABSTRACT

A bite block and airway assembly comprising a generally U-shaped resilient block having upper and lower teeth or gum-engaging surfaces and having an aperture formed centrally through the block between such surfaces and communicating between the interior and exterior of the block for matingly receiving and frictionally holding a tongue depressor type oral airway tube. The frictional engagement of the block with the airway tube provides slidable adjustability with respect to the depth of insertion of the tube while firmly holding the tube in any of a plurality of slidably adjustable positions. The tube-engaging aperture formed in the block is of oval shape for matingly and adjustably engaging any of a number of different types of airway tubes having different cross-sectional configurations. The device is usable as an oral protective device in electro-convulsive therapy or, alternatively, as an oral filler for the administration of gaseous anesthetic to edentulous patients.

2 Claims, 5 Drawing Figures

BITE BLOCK ASSEMBLY ADAPTED FOR ADJUSTABLE MOUNTING AND HOLDING OF ORAL AIRWAYS AND METHOD OF USING SAME

BACKGROUND OF THE INVENTION

This invention relates to improvements in bite block and airway assemblies adapted for use in electro-convulsive therapy of mental patients and also in the administration of gaseous anesthetic to edentulous patients.

During a seizure resulting from electro-convulsive therapy, an extremely strong mandibular contraction occurs requiring protection of the teeth and soft tissues of the mouth and lips. In additon, the possibility of respiratory emergencies during such therapy requires the maintenance of a free approach to the oral cavity and throat throughout the therapy so that resuscitative measures such as the administration of oxygen are possible. For these reasons various types of bite blocks equipped with airways have been used in the past for insertion into the mouth prior to the electroconvulsive therapy. Some of the bite block devices simply contain an air passageway through the mouth piece as shown in the Oberto U.S. Pat. No. 2,521,084. However such products provide inadequate airways partially obstructed by the patient's teeth and permit the patient's tongue to be drawn upwardly against the roof of the mouth shutting off the air passage into the throat. A number of bite block assemblies have attempted to solve this problem by providing a combination airway and tongue depressor tube which extends into the mouth and down the throat of the patient while the bite block is in place. One such assembly is shown in the Godfroy U.S. Pat. No. 2,882,893 wherein an airway-tongue depressor tube is formed integrally with the bite block. The primary problem with such type of assembly is that the depth of insertion of the tube into the throat is fixed when the bite block is in operative position in the mouth, such depth of insertion being insufficient for some patients and too great for other patients. Incorrect depth of insertion in turn can impair the effectiveness of the airway tube and cause serious patient discomfort. Another problem is that the airway tube is of a single fixed structure not necessarily adapted for the particular conduit functions desired, which are variable. For example there are a number of different types of airway-tongue depressor tubes presently on the market having different cross-sectional configurations and channels for performing different functions such as air supply and suction. Therapists may prefer different airway tube configurations for different situations, and an integral bite block and airway tube structure such as Godfroy's does not permit such flexibility.

Bite block assemblies which permit a separate or nonintegral tongue depressor-type airway tube to be inserted into the mouth and extend into the throat while the bite block is in operative position have also previously been used. However such assemblies do not positively hold the position of the airway tube while the bite block is in operative position nor maintain sufficient control of the degree of airway tube insertion throughout the therapy, thereby permitting operational difficulties and patient discomfort similar to those referred to in the previous paragraph.

In the somewhat unrelated field of administering a gaseous anesthetic to an edentulous patient by means of a face mask, it has been discovered that a bite block and airway assembly of the general type discussed above can overcome a certain special problem. The problem referred to is that the patient's absence of teeth tends to permit substantial looseness of the facial tissues in the area of the mouth and cheeks such that the face mask does not form an adequate seal with the face, causing harmful leakage between the anesthetic gas and the surrounding air. The use of a proper bite block and tongue depressor-type airway tube assembly during the administration of the anesthetic can solve the problem by the bite block's filling out the mouth region and correcting the looseness of tissue, thereby overcoming the otherwise defective fit of the face mask. The assembly however must be such as to overcome the foregoing disadvantages of present bite block and airway tube assemblies discussed above.

SUMMARY OF THE PRESENT INVENTION

The present invention is directed to a bite block and tongue depressor-type airway tube assembly comprising a generally U-shaped block of monolithic resilient material having upper and lower teeth or gum-engaging surfaces. These surfaces are formed to tilt toward one another in cross-section, tending to converge in an outward direction so as to prevent outward dislodgement of the bite block when the teeth are clamped together with great intensity, as occurs in electro-convulsive therapy. The surfaces are also wider apart adjacent the rear of the block than at the front to insure that the majority of the clamping pressure is absorbed by the molars rather than the frontal teeth which are more susceptible to splintering. An aperture is centrally formed through the front of the U-shaped block running between the upper and lower teeth-engaging surfaces and extending from front to rear in a direction between the two sides of the U-shaped block. The aperture matingly receives and frictionally holds a tongue depressor-type airway tube which extends through the aperture. The frictional engagement of the block with the tube provides slidable adjustability with respect to the depth of insertion of the tube while firmly holding the tube in any of a plurality of slidable positions. Preferably the aperture is of an oval shape for matingly and adjustably engaging any of a number of different types of airway tubes having different cross-sectional configurations.

In use, the assembly acts as an oral protective device in electro-convulsive therapy wherein the depth of insertion of the type of airway tube used can be adjusted to the most effective and comfortable position or removed entirely while the bite block is in place in the patient's mouth. Despite the adjustability, the bite block holds the airway tube firmly and reliably in whichever adjustable position is selected throughout the period of usage. The assembly may also be used in administering gaseous anesthetic by face mask to edentulous patients wherein the assembly fills out and firms up the otherwise loose tissue around the mouth and cheeks and ensures a proper sealing fit of the face mask with respect to the face, thereby avoiding leakage.

It is accordingly a primary objective of the present invention to provide a bite block assembly adapted to receive any of a number of different tongue depressor-type airway tubes and permit adjustability of depth of insertion of the airway tube with respect to the bite block while providing a firm, reliable, frictional engagement of the block with the tube in any of its adjustable positions so as to maintain the proper depth of insertion of the tube throughout use.

It is a further primary objective of the invention to ensure proper sealing fit of a face mask to an edentulous patient during the administration of gaseous anesthesia by utilizing such a bite block and airway tube assembly for filling out and firming up the facial tissues in the area of the mouth and cheeks of the patient.

The foregoing and other objectives, features and advantages of the present invention will be more readily understood upon consideration of the following detailed description of the invention taken in conjunction with the accompanying drawings.

DESCRIPTION OF THE PREFERRED EMBODIMENT

Figure 1:
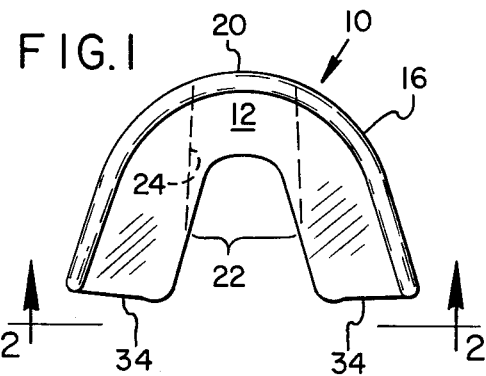
FIG. 1 is a top view of the preferred embodiment of the bite block of the present invention.
Figure 2:
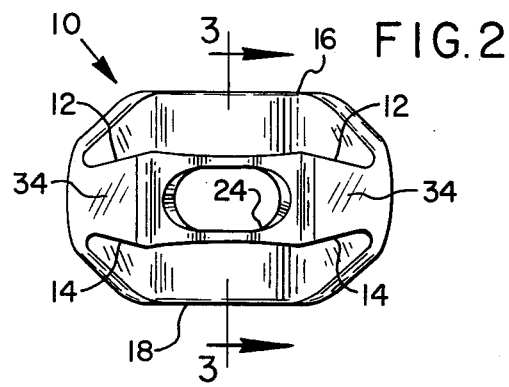
FIG. 2 is a rear view of the bite block taken along line 2—2 of FIG. 1.
Figure 3:
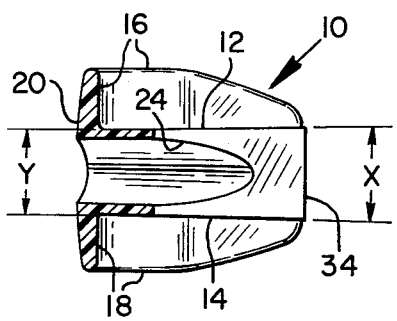
FIG. 3 is a longitudinal sectional view of the bite block taken along line 3—3 of FIG. 2.

With reference to FIGS. 1, 2 and 3, the bite block of the present invention comprises a generally U-shaped, molded monolithic block indicated generally as 10 made of a resilient, nontoxic material impervious to moisture such as polyurethane. The degree of resiliency may be variable depending upon usage of the block, less resiliency being desirable for electro-convulsive therapy where intense clamping force of the teeth is encountered than in the administration of gaseous anesthetics to edentulous patients, where much milder clamping force is encountered and protection of the tender gum tissue is desired. The bite block comprises an upper teeth or gum-engaging lateral surface 12 and a lower teeth or gum-engaging lateral surface 14, each formed in a U-shape with the base of the U at the front of the bite block and the sides of the U extending longitudinally rearwardly.

As seen in the rear view of FIG. 2, the surfaces 12 and 14 respectively are tilted in transverse cross-section with respect to one another so as to tend to converge in an exterior direction. This feature is very useful in preventing the bite block from being dislodged outwardly from its operative position by the intense clamping force of the teeth normally experienced in electro-convulsive therapy. Rather the cross-sectional wedge shape resulting from the tilt of the surfaces 12 and 14 with respect to one another utilizes the clamping force to retain the block against outward dislodgement. As will be seen, the position of the bite block in the patient's mouth also determines the depth of insertion of the airway into the patient's mouth, so that the prevention of outward dislodgement of the block has special significance not only with respect to protection of the teeth but also with respect to the maintenance of proper airway positioning.

To prevent against inward dislodgement or slippage of the bite block with respect to the patient's mouth, upwardly and downwardly extending flanges 16 and 18 respectively located at the outer edges of the respective teeth-engaging surfaces 12 and 14 each having a rearwardly opening U-shape are provided to engage the outer sides of the teeth or gums.

As is best seen in FIG. 3, the vertical distance "x" separating the upper and lower teeth-engaging surfaces 12 and 14 resectively at the rearmost ends of the surfaces is preferably greater than the corresponding vertical distance "y" separating the two surfaces at the front of the block. The purpose is primarily to ensure that the majority of the mandibular clamping force during electro-convulsive therapy is borne by the patient's molars rather than his frontal teeth, the molars being much more resistant to splintering. Moreover, since the airway channel to be described hereafter passes between the upper and lower teeth-engaging surfaces at the front of the block, high teeth clamping force at that location should also be avoided so as to prevent any tendency of the teeth to close or compress the airway channel.

Figure 4:
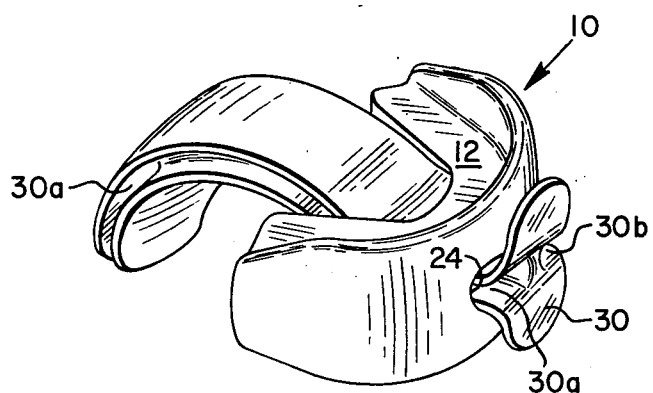
FIG. 4 is an assembly drawing showing the bite block with a typical tongue depressor-type airway slidably inserted through the bite block and held in operative position thereby.
Figure 5:
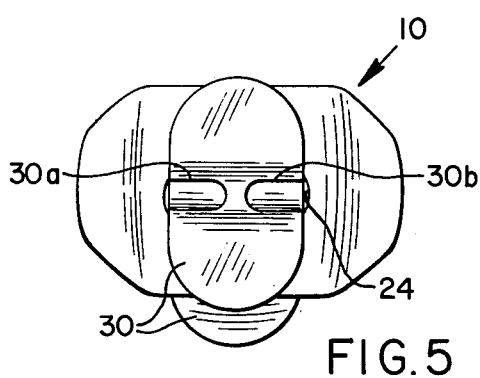
FIG. 5 is a front view of the assembly of FIG. 4.

Extending from the front 20 of the exterior of the bite block 10 in a rearward direction between the upper and lower teeth-engaging surfaces 12 and 14, and emerging in the interior space 22 between the two sides of the U-shaped block 10, is an aperture 24 of generally oval cross-section. Preferably the maximum height of the aperture cross-section is one centimeter and maximum width is two centimeters. It has been found that the oval-shaped aperture is adapted for slidably and frictionally engaging virtually all of the different types of tongue depressor-type airway tubes or airway channels which might be desired under variable conditions. For example, the tongue depressor-type airway channel 30 shown in FIGS. 4 and 5 is a preformed device of arcuate shape having two separate channels 30a and 30b formed therein for performing two separate gas-conducting functions, such as providing oxygen through one channel and suction through the other. This particular type of tongue-depressor airway requires that flexible tubes be inserted in the respective channels 30a and 30b, such tubes running along the sides of the device and conforming to the arcuate shape of the airway 30. Other such tongue depressor-type airways would also have the preformed arcuate tongue-depressor shape, but might be formed as a single closed channel or tube, or a tube having multiple channels within the tube. Regardless of the type of such tongue-depressor airway, the oval-shaped aperture 24 coupled with the resilient material of the bite block 10 is capable of matingly and frictionally accepting the insertion of the airway while permitting longitudinal sliding of the airway device with respect to the bite block for adjustment of the degree of insertion of the airway device. However to provide this slidability, it is important that the walls forming the aperture not extend too far rearwardly, and certainly no further than the rearmost ends 34 of the two sides of the U-shaped block 10, as opposed to those bite blocks previously discussed which have integral airway tubes. Despite the slidability permitted by the present invention, the frictional engagement permits the bite block to hold the airway firmly and reliably with respect to the block in any of its slidably adjustable positions.

In use, the appropriate airway device such as 30 is inserted through the aperture 24 in the bite block 10 and the bite block and airway assembly is placed in the patient's mouth. Longitudinal adjustment of the degree of insertion of the airway 30 can be accomplished either while the bite block remains in the patient's mouth or by removing the bite block, sliding the airway and replacing the bite block in the patient's mouth. In either case the objective is to adjust the airway to a depth such that the inserted end of the airway is comfortably adjacent the throat of the patient and communicating between the exterior and interior of the bite block when the block is operatively inserted in the patient's mouth.

For the administration of gaseous anesthesia to edentulous patients by means of a face mask, the bite block serves as a filler to firm up and fill out facial tissues in the mouth and cheek area when placed in the patient's mouth prior to the application of the face mask. The resultant peripheral seal of the mask with the patient's face when the mask is subsequently placed on the face over the block and airway assembly can thereby be ensured to be leakproof.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A bite block and airway assembly for inserting between the teeth of a patient for absorbing the force of mandibular contractions comprising:
   (a) a monolithic block of resilient material formed in a U-shaped such that the exterior of the block is generally convex and the interior of the block is generally concave;
   (b) respective upwardly and downwardly facing teeth-engaging surfaces vertically spaced from one another extending longitudinally along each of the two sides of the U-shaped block wherein said respective upwardly and downwardly facing teeth-engaging surfaces tilt toward one another in transverse cross section, tending to converge in a direction toward the exterior of said block, so as to define wedge-shaped resilient material means therebetween for effectively resisting and withstanding the force of said mandibular contractions and directing said force against the wedge-shaped means in a direction toward the interior of the block to retain the block against outward dislodgment from the teeth;
   (c) means defining an aperture formed through a central portion of the U-shaped block which joins the two sides thereof together, said aperture extending between the exterior and interior of said block between the levels of said upwardly and downwardly facing teeth-engaging surfaces; and
   (d) preformed, elongate, arcuate-shaped airway means slidably inserted through said aperture for conducting gas between the exterior and interior of said block while depressing the tongue of said patient, said airway means and aperture having mating surface means for frictionally and slidably engaging one another in any of a plurality of positions along the length of said airway means so as to permit slidable adjustment of said airway means with respect to said block.

2. A bite block and airway assembly for inserting between the teeth of a patient for absorbing the force of mandibular contractions comprising:
   (a) a monolithic block of resilient material formed in a U-shape such that the exterior of the block is generally convex and the interior of the block is generally concave;
   (b) respective upwardly and downwardly facing teeth-engaging surfaces vertically spaced from one another extending longitudinally along each of the two sides of the U-shaped block, said respective upwardly and downwardly facing teeth-engaging surfaces tilting toward one another in transverse cross section tending to converge in a direction toward the exterior of said block, so as to define wedge-shaped resilient material means therebetween for effectively resisting and withstanding the force of said mandibular contractions and directing said force against the wedge-shaped means in a direction toward the interior of the block to retain the block against outward dislodgment from the teeth; and
   (c) means defining an aperture formed through a central portion of the U-shaped block which joins the two sides thereof together, said aperture extending between the exterior and interior of said block between the levels of said upwardly and downwardly facing teeth-engaging surfaces.

* * * * *